United States Patent [19]

Hochstetler et al.

[11] 4,250,061

[45] Feb. 10, 1981

[54] 2-ACETYL-1,3,3,4,4-PENTAMETHYLCYCLOPENTENE AS A FRAGRANCE MATERIAL

[75] Inventors: Alan R. Hochstetler; Glen R. Fredericks, both of Clifton, N.J.; Erlinda F. Golle, Bronx, N.Y.

[73] Assignee: Givaudan Corporation, Clifton, N.J.

[21] Appl. No.: 49,833

[22] Filed: Jun. 18, 1979

Related U.S. Application Data

[63] Continuation-in-part of Ser. No. 935,443, Aug. 21, 1978, abandoned.

[51] Int. Cl.[3] .......... A61K 7/46

[52] U.S. Cl. .......... 252/522 R; 424/65

[58] Field of Search .......... 252/522 R; 424/65

[56] References Cited

U.S. PATENT DOCUMENTS

| | | | |
|---|---|---|---|
| 3,932,517 | 1/1976 | Naegeli | 252/522 |
| 3,937,723 | 2/1976 | Elte | 252/522 |
| 3,963,675 | 6/1976 | Naegeli | 252/522 |
| 4,173,585 | 11/1979 | Yoshida et al. | 252/522 |

FOREIGN PATENT DOCUMENTS

| | | | |
|---|---|---|---|
| 68936 | 9/1969 | Fed. Rep. of Germany | 252/522 |
| 2094264 | 2/1972 | France | 252/522 |
| 7003145 | 9/1970 | Netherlands | 252/522 |
| 7609055 | 8/1975 | Netherlands | 252/522 |
| 1437153 | 5/1976 | United Kingdom | 252/522 R |
| 1530118 | 10/1978 | United Kingdom | 252/522 R |

OTHER PUBLICATIONS

Kolobielski, Ann. de Chim., 1955, 10, pp. 271–314.

Arctander, perfume & Flavor Chemicals, 1969, Nr. 1869 and Nr. 1992.

Derwent Abstract, 8/1975, DT2536–2543.

*Primary Examiner*—Dale R. Ore

*Attorney, Agent, or Firm*—Robert F. Tavares; Thomas Cifelli, Jr.

[57] ABSTRACT

Odorant compositions prepared by adding thereto olfactorily effective amounts of substantially pure 2-acetyl-1,3,3,4,4-pentamethylcyclopentene.

17 Claims, No Drawings

2-ACETYL-1,3,3,4,4-PENTAMETHYLCYCLOPENTENE AS A FRAGRANCE MATERIAL

RELATED U.S. APPLICATION DATA

This is a continuation-in-part of Ser. No. 935,443 filed Aug. 21, 1978, now abandoned.

THE INVENTION

This invention teaches methods for preparing fragrance compositions utilizing 2-acetyl-1,3,3,4,4-pentamethylcyclopentene, a known compound which can be prepared according to the procedure described in Ann. de Chim., 10, 271 (1955). The prior art makes no mention of its odor characteristics or of any use in odorant compositions.

The 2-acetyl-1,3,3,4,4-pentamethylcyclopentene has an odor which can be described as warm, spicy, peppery, camphoraceous and woody. Each of these notes can be used to good advantage in a wide variety of fragrance compositions. It has been found that by judiciously blending this compound with other ingredients, certain notes can be enhanced.

Another important characteristic of the compound is its ability to blend with other ingredients and provide "roundness" and "lift" to the final fragrance composition. The terms "roundness" and "lift" are terms of art used by the perfumer. "Roundness" refers to that quality in a fragrance composition which gives it a pleasant blended odor without the odor of any individual chemical "standing out" from the total bouquet of the fragrance composition. The term "lift" refers to that quality in the finished fragrance composition which gives it the initial impact and odor intensity when first perceived by the olfactory senses. Obviously, any perfume must present a smooth, blended, total bouquet and have a positive initial impact on the consumer if it is to be commercially acceptable.

The versatility of the 2-acetyl-1,3,3,4,4-pentamethylcyclopentene can be illustrated in a variety of ways. In florals it provides "roundness" and "lift" to the final fragrance composition making the fragrance more reminiscent of the natural flower.

Each floral has its own peculiar characteristics and the perfumer, by judicious blending, can take advantage of certain characteristic notes of the 2-acetyl-1,3,3,4,4-pentamethylcyclopentene. In a carnation type fragrance, where spicy notes are desirable, the addition of the 2-acetyl-1,3,3,4,4-pentamethylcyclopentene enhances and contributes to the spicy and floral quality of the finished fragrance. In orris or violet type florals, where woody characteristics are more important, the addition of the 2-acetyl-1,3,3,4,4-pentamethylcyclopentene contributes to the woody notes providing a fragrance which is more "rounded" and closer to the natural odor.

The outstanding characteristic of the 2-acetyl-1,3,3,4,4-pentamethylcyclopentene is its blending quality, i.e. its ability to tie together a number of individual odor characteristics to provide an integrated blend.

This ability to blend and provide "roundness" and "lift" to the final fragrance composition has been noted above. This ability is most dramatically illustrated in a lavandin type fragrance wherein the 2-acetyl-1,3,3,4,4-pentamethylcyclopentene, which has no herbal notes of its own, blends the herbal notes of that fragrance to provide a finished, integrated effect.

The blending characteristics are also useful in colognes. Many colognes have green, citrus, amber, woody and herbal notes. Addition of the 2-acetyl-1,3,3,4,4-pentamethylcyclopentene blends the individual notes providing "roundness" and "lift" to the final composition.

Compounds which have structures closely related to the 2-acetyl-1,3,3,4,4-pentamethylcyclopentene (I) of this invention do not have the desirable olfactory properties possessed by I. For example, the 2-acetyl-3,3,5-trimethylcyclopentene (II)

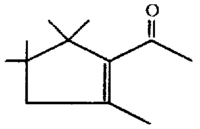

I

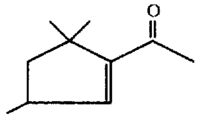

II

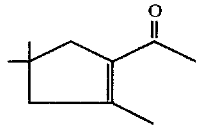

III was described by the perfumers as having a minty, leafy-green odor with an undesirable pungent note. The 2-acetyl-1,4,4-trimethylcyclopentene (III) was described by the perfumers as having a minty, plastic, metallic, earthy odor with an undesirable pungent note that was even more marked than that of II.

Whereas I has the ability to tie together odor characteristics of a fragrance composition to provide an integrated blend or "rounded" fragrance, the substitution of II or III had the opposite effect. The blending quality was not there and the characteristic odors of II and III stood out in the fragrance mixture resulting in a detrimental, rather than a beneficial effect.

The perfume arts are, of course, subjective. The amounts used, as well as the scope of such use, will depend ultimately upon the imagination and personal preferences of the perfumer. Amounts used will also depend on the type of fragrance and it is well within the skill of the perfumer to add the compound in varying amounts to determine the preferred range.

For the most part, the 2-acetyl-1,3,3,4,4-pentamethylcyclopentene can be used in fragrance formulations in a practical range from as low as 0.01 percent to 30 percent with 0.3 percent to 25 percent being preferred. This will vary, of course, depending upon the type of fragrance formula involved. Concentrations above 30 percent even as high as 80 or 90 percent, may be used successfully for special effects.

The compounds can be used to prepare fragrance bases for the preparation of perfumes and toilet waters by adding the usual alcoholic and aqueous diluents thereto. Approximately 15-20% by weight of base would be used for perfumes and approximately 3-5% for toilet waters.

Similarly, the base compositions can be used to odorize soaps, detergents, cosmetics, or the like. In these instances, a base concentration of from about 0.5 to about 2% by weight can be used.

ILLUSTRATION OF THE PREFERRED EMBODIMENTS

The following examples are provided for the sole purpose of illustrating the preferred embodiments of this invention and they should not be construed as limiting. Unless otherwise indicated, perfume ingredients are given in parts per thousand by weight.

Where the material used is better known by its common name, trademark or tradename, such a name is used with the chemical name being given in parentheses.

EXAMPLE I

The use of 2-acetyl-1,3,3,4,4-pentamethylcyclopentene in floral compositions is illustrated by using it in the following carnation base.

Carnation

| Components | Parts |
|---|---|
| 10% Aldehyde C-11 (10-undecenal) | 10 |
| Amyl Salicylate (isoamyl o-hydroxybenzoate) | 100 |
| Baccartol ®* | 50 |
| Benzyl Isoeugenol | 30 |
| Cinnamic Alcohol | 75 |
| Cinnamon Leaf Seychelles | 5 |
| Copaiba Oil | 40 |
| Eugenol | 50 |
| Folrosia ®(p-isopropylcyclohexanol) | 90 |
| Isoeugenol | 50 |
| Methyl Isoeugenol | 20 |
| Methyl Undecylenate | 10 |
| Musk Ambrette | 15 |
| Nutmeg Oil | 10 |
| Phenyl Ethyl Alcohol | 100 |
| Rhodinol 70 (mixture of α (~70%) and β (~30%) citronellol) | 200 |
| Roseacetol (trichloromethylphenylcarbinyl acetate) | 30 |
| Valspice ® (2-methyoxy-4-methylphenol) | 5 |
| 4-Acetyl-1,1-dimethyl-6-t-butylindan | 50 |
| Ylang-Ylang #3 | |
| 2-Acetyl-1,3,3,4,4-pentamethylcyclopentene (I) | 10 |
| | 1000 |

*Givaudan Trademark for a condensation product of citronella oil and acetone.

The addition of 2-acetyl-1,3,3,4,4-pentamethylcyclopentene to the above carnation composition greatly enhances the spicy character of the carnation, results in a more balanced note, and imparts "roundness" and a great "lift" to the total composition. Without the 2-acetyl-1,3,3,4,4-pentamethylcyclopentene the formulation is flat, incomplete and lacks the quality of a finished fragrance.

EXAMPLE II

The following example illustrates the ability of 2-acetyl-1,3,3,4,4-pentamethylcyclopentene to blend the notes in a herbal composition such as lavandin synthetic.

Lavandin Synthetic

| Components | Parts |
|---|---|
| Linalool | 100 |
| Isobornyl Acetate | 100 |
| Lavandin Intensifier* | 20 |
| Linalyl Acetate | 300 |
| Lavandulol | 50 |
| Lavander 38/42** | 150 |
| Coumarin | 50 |
| 2-Acetyl-1,3,3,4,4-pentamethylcyclopentene (I) | 230 |
| | 1000 |

*Lavandin Intensifier is a blend consisting of 5.0 parts of methyl amyl ketone, 20.0 parts of methyl hexyl ketone, 10.0 parts of methyl nonyl ketone, and 0.5 parts of butyl acetate.

**A liquid perfume base consisting primarily of linalool and linalool actate used in finished perfumes, colognes, cosmetics and soaps.

The composition without the 2-acetyl-1,3,3,4,4-pentamethylcyclopentene is incomplete and is essentially a potpourri of individual odorants. The alkyl ketone notes stand out individually.

Addition of about 20–25% of the 2-acetyl-1,3,3,4,4-pentamethylcyclopentene effects a blending of these individual notes into an integrated whole. The herbal notes are blended and the final fragrance is "rounded", complete and exhibits the natural herbal character of the natural oil.

EXAMPLE III

The use of 2-acetyl-1,3,3,4,4-pentamethylcyclopentene in a cologne base is illustrated by the following formulation.

Cologne Base

| Component | Parts |
|---|---|
| Acetate PA (Allyl phenoxyacetate) | 10 |
| Ambrate ® (Acetoxy-2-sec. butyl-1-ethynylcyclohexane) | 50 |
| Benzyl Acetate Extra | 40 |
| Herboral ®* | 30 |
| Lemon Oil California | 230 |
| Lime Distilled | 100 |
| Linalool | 50 |
| Linalyl Acetate | 150 |
| Dipropylene Glycol | 120 |
| Petitgrain oil (South American) | 30 |
| Phenyl Ethyl Alcohol | 50 |
| Sandela ®** | 30 |
| Terpineol Extra | 30 |
| 2-Acetyl-1,3,3,4,4-pentamethylcyclopentene (I) | 80 |
| | 1000 |

*Givaudan Trademark for a product which is primarily acetylated citronellal.
**Givaudan Trademark for a polycyclic alcohol having a sandalwood odor.

The above cologne base without the 2-acetyl-1,3,3,4,4-pentamethylcyclopentene is incomplete. While it includes ingredients contributing green, citrus, amber, woody, and herbal notes, the individual notes stick out.

Addition of the 2-acetyl-1,3,3,4,4-pentamethylcyclopentene to the cologne base blends the composition to give an integrated bouquet. The citrus notes, while enhanced, are "rounded" and blended into the total composition.

EXAMPLE IV

The use of 2-acetyl-1,3,3,4,4-pentamethylcyclopentene in a woody, floral type composition is illustrated in the following orris base.

Orris Base

| Components | Parts |
|---|---|
| α-Ionone | 225 |
| Raldeine γ-pure | 225 |
| Anisic Aldehyde | 30 |
| Terpineol | 200 |
| Heliotropine | 30 |
| Ethyl Vanillin | 10 |

-continued

| Orris Base | |
|---|---|
| Components | Parts |
| Musk Ketone | 10 |
| Coumarin | 10 |
| Dipropylene Glycol | 95 |
| Oris Absolute Resin | 20 |
| Concrete Orris Abs. | 30 |
| Vetiver | 25 |
| Cedryl Acetate Crystals | 20 |
| Carrot Seed Oil 10% in DEP | 10 |
| Ionone | 10 |
| 2-Acetyl-1,3,3,4,4-pentamethylcyclopentene (I) | 50 |

The 2-acetyl-1,3,3,4,4-pentamethylcyclopentene in the above orris base enhances the orris character and imparts more "roundness" and "lift" into the finished composition.

EXAMPLE V

The use of 2-acetyl-1,3,3,4,4-pentamethylcyclopentene in a fourgere composition is illustrated below.

| Fougere | |
|---|---|
| Components | Parts |
| Amyl Salicylate | 130 |
| Anisic Aldehyde | 50 |
| Benzoin Siam Soluble Resin | 30 |
| Benzyl Acetate Extra | 100 |
| Bergamot 65 GD* | 350 |
| Coumarin | 20 |
| Dipropylene Glycol | 103 |
| Estragole (p-allylanisole) | 5 |
| Folrosia® (p-isopropylcyclohexanol) | 10 |
| Geranium Bourbon | 30 |
| Heliotropine Crystals | 50 |
| Citral | 2 |
| Musk Ambrette | 30 |
| Nerol Prime | 10 |
| Phenyl Ethyl Alcohol | 30 |
| Treemoss 50% in Dipropylene glycol | 4 |
| Thymol 10% in Dipropylene glycol | 1 |
| Vanillin USP | 5 |
| 2-Acetyl-1,3,3,4,4-pentamethylcyclopentene (I) | 40 |
| | 1000 |

*A liquid perfume base used in finished perfumes, colognes, cosmetics and soaps.

The 2-acetyl-1,3,3,4,4-pentamethylcyclopentene in the above fougere base adds body, lift, and intensity. It imparts to the total composition, a more natural quality.

We claim:

1. A method for improving the odor of fragrance compositions which comprises adding thereto an amount of 2-acetyl-1,3,3,4,4-pentamethylcyclopentene sufficient to put its concentration in the fragrance base between 0.01% and 30% of the fragrance base.

2. The method of claim 1 wherein the amount would be from 0.3% to 25% of the fragrance base.

3. The method of claim 1 wherein the 2-acetyl-1,3,3,4,4-pentamethylcyclopentene is added to impart "roundness" and "lift".

4. The method of claim 1 wherein the fragrance composition to be improved is of the floral type.

5. The method of claim 4 wherein the floral is of the carnation type.

6. The method of claim 4 wherein the floral is of the orris or violet type.

7. The method of claim 1 wherein the fragrance composition to be improved is of the lavandin type.

8. The method of claim 1 wherein the fragrance composition to be improved is of the citrus type.

9. The method of claim 1 wherein the fragrance composition to be improved is of the fougere type.

10. A fragrance composition which comprises an amount of 2-acetyl-1,3,3,4,4-pentamethylcyclopentene sufficient to put its concentration between 0.01% and 30% of the total fragrance base.

11. The composition of claim 10 wherein the 2-acetyl-1,3,3,4,4-pentamethylcyclopentene is from 0.3% to 25% of the fragrance base.

12. A composition of claim 10 having a floral odor.

13. A composition of claim 12 having a carnation odor.

14. A composition of claim 12 having a violet or orris type odor.

15. A composition of claim 10 having a lavandin type odor.

16. A composition of claim 10 having a citrus type odor.

17. A composition of claim 10 having a fougere type odor.

* * * * *